(12) United States Patent
Kasai (10) Patent No.: US 9,095,254 B2
(45) Date of Patent: Aug. 4, 2015

(54) ENDOSCOPE APPARATUS AND BENDING CONTROL METHOD OF ENDOSCOPE APPARATUS

(75) Inventor: Yoichiro Kasai, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 154 days.

(21) Appl. No.: 13/248,393

(22) Filed: Sep. 29, 2011

(65) Prior Publication Data

US 2013/0085336 A1 Apr. 4, 2013

(51) Int. Cl.
*A61B 1/005* (2006.01)
(52) U.S. Cl.
CPC ............. *A61B 1/0057* (2013.01); *A61B 1/0053* (2013.01)
(58) Field of Classification Search
CPC .... A61B 1/005; A61B 1/0053; A61B 1/0057; A61B 1/008
USPC .................................................. 600/145–152
See application file for complete search history.

(56) References Cited

U.S. PATENT DOCUMENTS

| | | | | |
|---|---|---|---|---|
| 4,794,912 A | * | 1/1989 | Lia ................................ | 600/152 |
| 4,832,473 A | * | 5/1989 | Ueda ............................. | 600/152 |
| 4,962,751 A | * | 10/1990 | Krauter ......................... | 600/152 |
| 5,014,515 A | * | 5/1991 | Krauter ......................... | 600/152 |
| 5,179,934 A | * | 1/1993 | Nagayoshi et al. ........... | 600/152 |
| 5,897,488 A | * | 4/1999 | Ueda ............................. | 600/151 |
| 2006/0178563 A1 | * | 8/2006 | Hirata et al. .................. | 600/152 |
| 2006/0207419 A1 | * | 9/2006 | Okazaki et al. ............... | 91/35 |

FOREIGN PATENT DOCUMENTS

| | | |
|---|---|---|
| JP | 05-031069 A | 2/1993 |
| JP | 6-67378 B2 | 8/1994 |
| JP | 2008-279099 A | 11/2008 |

OTHER PUBLICATIONS

Japanese Office Action dated Dec. 3, 2013, in counterpart Japanese Application No. 2010-105553.

* cited by examiner

*Primary Examiner* — Thomas J Sweet
*Assistant Examiner* — Kevin G Barry, III
(74) *Attorney, Agent, or Firm* — Holtz, Holtz, Goodman & Chick PC (57) ABSTRACT

Provided is an endoscope apparatus that includes: a bending portion that bends in at least one direction; bending wires that are each connected to the bending portion; actuators that are connected to proximal ends of the bending wires, respectively, and that contract or expand by means of air pressure; electromagnetic valves that are provided between the actuators and a gas supply source that supplies air, respectively, and that adjust pressures applied to the actuators; and a control section that controls the electromagnetic valves. Each bending wire has slack therein when the actuators are in an atmospheric pressure state. The control section controls the electromagnetic valves so as to subject the actuators to initial pressurization until the slack of each bending wire disappears.

15 Claims, 10 Drawing Sheets

FIG.2A

POWER SUPPLY OFF

FIG.2B

NEUTRAL STATE
(INITIAL PRESSURIZATION)

FIG.2C

U DIRECTION BENDING

| MOVEMENT OF DISTAL END PORTION | ELECTROMAGNETIC VALVE | | | | | | | |
|---|---|---|---|---|---|---|---|---|
| | 15a | 16a | 15b | 16b | 15c | 16c | 15d | 16d |
| INITIAL PRESSURIZATION TIME | ON | P | ON | P | ON | P | ON | P |
| BENDING TO U DIRECTION TIME | ON | P | P | OFF | ON | OFF | ON | OFF |
| BENDING TO D DIRECTION TIME | P | OFF | ON | P | ON | OFF | ON | OFF |
| BENDING TO R DIRECTION TIME | ON | OFF | ON | OFF | ON | P | P | OFF |
| BENDING TO L DIRECTION TIME | ON | OFF | ON | OFF | P | OFF | ON | P |
| RETAINING BENDING ANGLE TIME | ON | OFF | ON | OFF | ON | OFF | ON | OFF |

| MOVEMENT OF DISTAL END PORTION | ELECTROMAGNETIC VALVE | | | | | | | |
|---|---|---|---|---|---|---|---|---|
| | 15a | 16a | 15b | 16b | 15c | 16c | 15d | 16d |
| INITIAL PRESSURIZATION TIME | ON | OFF | ON | OFF | ON | OFF | ON | OFF |
| BENDING TO U DIRECTION TIME | ON | P | P | OFF | ON | OFF | ON | OFF |
| BENDING TO D DIRECTION TIME | P | OFF | ON | P | ON | OFF | ON | OFF |
| BENDING TO R DIRECTION TIME | ON | OFF | ON | OFF | ON | P | P | OFF |
| BENDING TO L DIRECTION TIME | ON | OFF | ON | OFF | P | OFF | ON | P |
| RETAINING BENDING ANGLE TIME | ON | OFF | ON | OFF | ON | OFF | ON | OFF |

ENDOSCOPE APPARATUS AND BENDING CONTROL METHOD OF ENDOSCOPE APPARATUS

BACKGROUND OF THE INVENTION

1. Field of the Invention

The present invention relates to an endoscope apparatus and a bending control method of an endoscope apparatus. More particularly, the present invention relates to an endoscope apparatus and a bending control method of an endoscope apparatus in which bending of a distal end of an insertion portion is controlled by controlling pressures applied to actuators that expand and contract by means of a fluid pressure.

2. Description of the Related Art

A large variety of endoscope apparatuses that insert an insertion portion into a subject and observe the inside of the subject have been conventionally available. In these endoscope apparatuses, a bending portion is provided at a proximal end of a distal end portion of the insertion portion, and the observation direction can be oriented in a desired direction by performing a bending operation with respect to the bending portion.

For example, among such endoscope apparatuses that include a bending portion, an endoscope apparatus has been proposed that, when bending the bending portion, causes the bending portion to bend by utilizing air pressure (for example, see Japanese Examined Patent Application Publication No. 6-67378).

In an endoscope apparatus that causes a bending portion to bend by utilizing air pressure in this manner, a gas supply source and an air chamber of the bending portion are connected to each other by a thin air tube, and the amount of bending is controlled by detecting a pressure of an actuator such as an artificial muscle by means of a pressure sensor that is provided in a connection portion between the air tube and an electromagnetic valve.

SUMMARY OF THE INVENTION

An endoscope apparatus according to one aspect of the present invention includes: a bending portion that bends in at least one direction; two bending wires that are each connected to the bending portion; two actuators that are connected to proximal ends of the two bending wires, respectively, and that contract or expand by means of a fluid pressure; two pressure adjusting sections that are provided between the two actuators and a fluid supply source that supplies a fluid to the two actuators, respectively, and that adjust pressures applied to the two actuators; and a control section that controls the two pressure adjusting sections; wherein: each of the two bending wires has slack therein when the two actuators are in an atmospheric pressure state; and the control section controls the two pressure adjusting sections so as to subject the two actuators to an initial pressurization until the slack of each of the two bending wires disappears.

Further, a bending control method of an endoscope apparatus according to another aspect of the present invention is a bending control method of an endoscope apparatus that includes: a bending portion that bends in at least one direction; two bending wires that are each connected to the bending portion; two actuators that are connected to proximal ends of the two bending wires, respectively, and that contract or expand by means of a fluid pressure; and two pressure adjusting sections that are provided between the two actuators and a fluid supply source that supplies a fluid to the two actuators, respectively, and that adjust pressures applied to the two actuators; wherein the bending control method includes: detecting that a power supply of the endoscope apparatus is turned on; and controlling the two pressure adjusting sections so as to subject the two actuators to an initial pressurization until slack that each of the two bending wires has therein when the two actuators are in an atmospheric pressure state disappears.

BRIEF DESCRIPTION OF THE DRAWINGS

FIG. 8 is a flowchart for describing an example of a process flow when the power supply of the endoscope apparatus is turned on;

DETAILED DESCRIPTION OF THE PREFERRED EMBODIMENTS

An embodiment of the present invention is described in detail hereunder with reference to the accompanying drawings.

Figure 1:
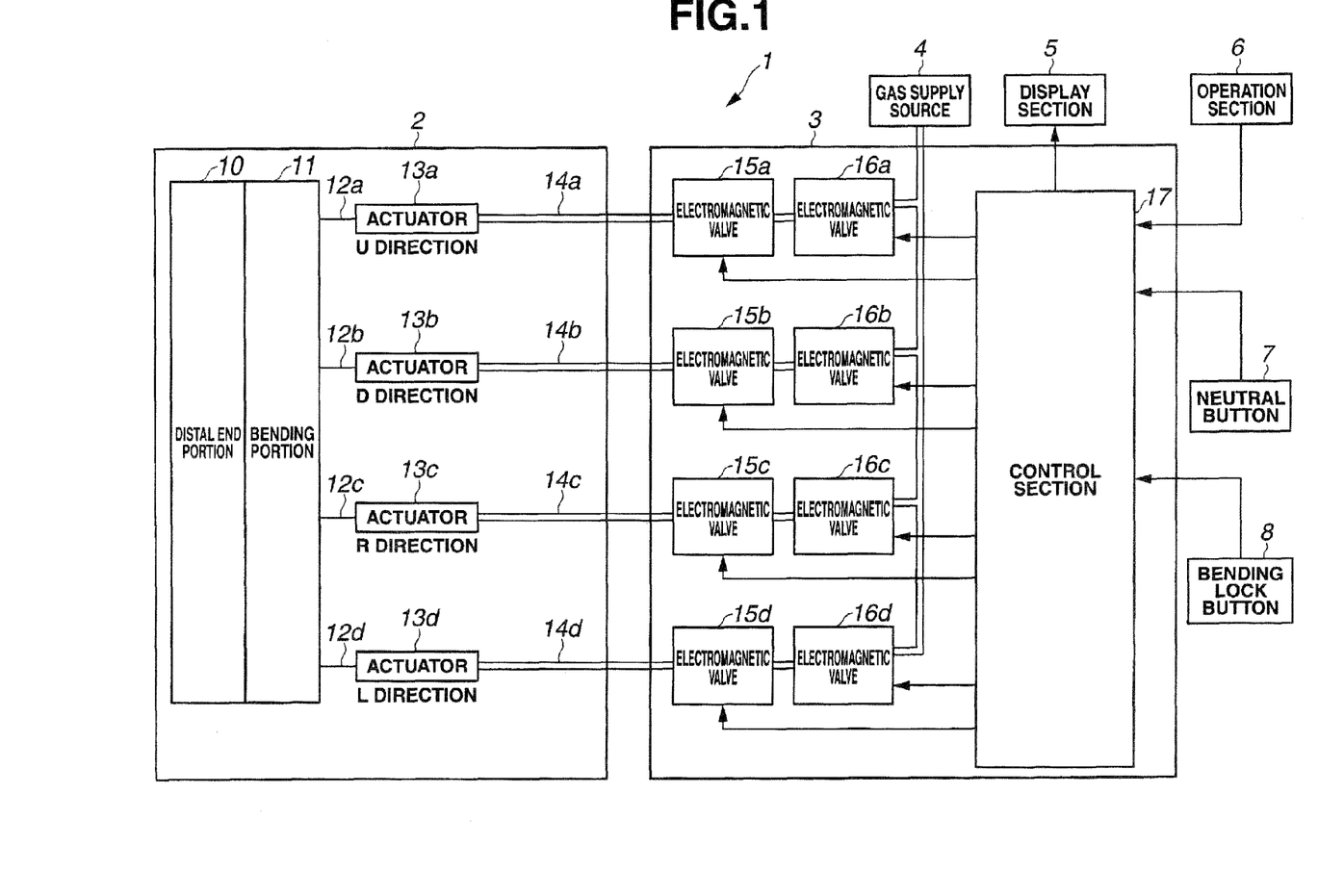
FIG. 1 is a view for describing the configuration of an endoscope apparatus according to an embodiment of the present invention.
Figure 2A:
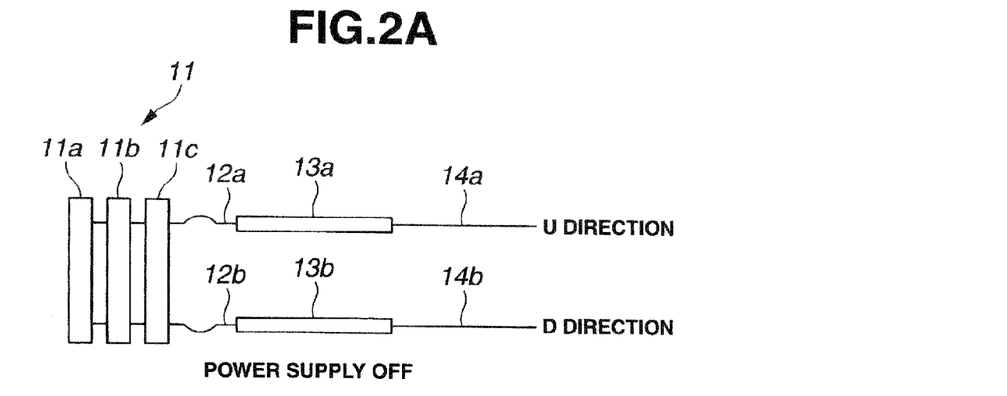
FIG. 2A is a schematic view for describing the configuration of a bending portion of the endoscope apparatus when a power supply is off.
Figure 2B:
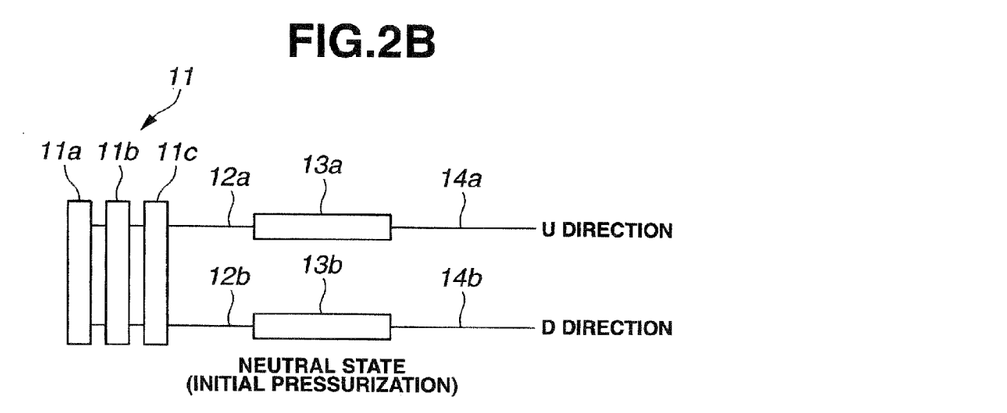
FIG. 2B is a schematic view for describing the configuration of the bending portion of the endoscope apparatus when in a neutral state (at a time of initial pressurization)
Figure 2C:
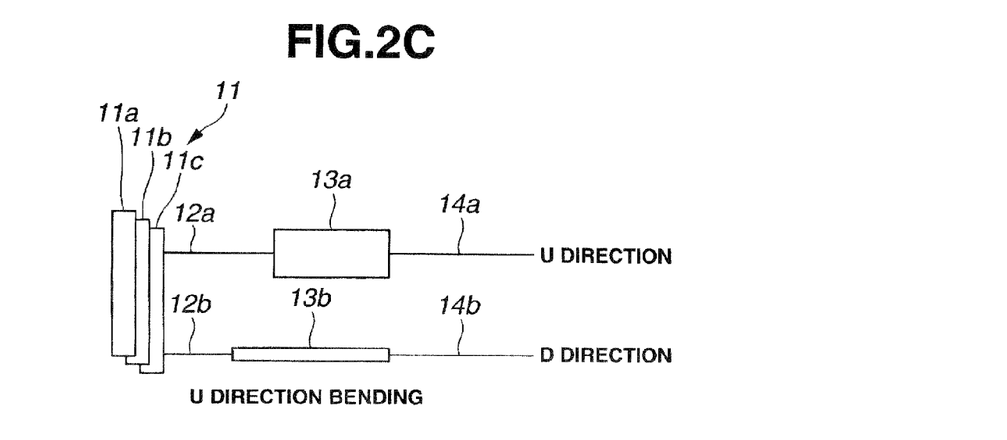
FIG. 2C is a schematic view for describing the configuration of the bending portion of the endoscope apparatus when bending the bending portion in a U direction.

First, the configuration of an endoscope apparatus according to the present embodiment is described based on FIG. 1 to FIG. 2C.

FIG. 1 is a view for describing the configuration of the endoscope apparatus according to the present embodiment. FIG. 2A is a schematic view for describing the configuration of a bending portion of the endoscope apparatus when a power supply is off. FIG. 2B is a schematic view for describing the configuration of the bending portion of the endoscope apparatus when in a neutral state (at a time of initial pressurization). FIG. 2C is a schematic view for describing the configuration of the bending portion of the endoscope apparatus when bending the bending portion in a U direction.

As shown in FIG. 1, an endoscope apparatus 1 includes an insertion portion 2, an endoscope main body 3, a gas supply source 4, a display section 5, an operation section 6, a neutral button 7, and a bending lock button 8.

The insertion portion 2 includes a distal end portion 10, a bending portion 11, bending wires 12a to 12d that correspond to upward, downward, right, and left directions, respectively, actuators 13a to 13d that correspond to the upward, downward, right, and left directions, respectively, and air tubes 14a to 14d that correspond to the upward, downward, right, and left directions, respectively.

The endoscope main body 3 includes the air tubes 14a to 14d that correspond to the upward, downward, right, and left directions, respectively, first electromagnetic valves 15a to 15d that correspond to the upward, downward, right, and left directions, respectively, second electromagnetic valves 16a to 16d that correspond to the upward, downward, right, and left directions, respectively, and a control section 17.

The gas supply source 4 is a gas cylinder or air piping or the like, and feeds air to the actuators 13a to 13d through the air tubes 14a to 14d.

Unshown image pickup means is provided in the distal end portion 10. An image pickup signal that is picked up by the image pickup means is sent to an unshown image processing apparatus and subjected to image processing, and is thereafter displayed on the display section 5.

The bending portion 11 is provided at the proximal end of the distal end portion 10. As shown in FIG. 2A, the bending portion 11 has a plurality of bending pieces. In this case, the bending portion 11 has three bending pieces 11a to 11c. In this connection, although only the U and D directions are illustrated in FIG. 2A to FIG. 2C, a similar configuration as that for the U and D directions also applies with respect to R and L directions.

Among the three bending pieces 11a to 11c, the bending wires 12a to 12d are connected to the bending piece 11a that is on the distal end portion 10 side. As shown in FIG. 2A, the bending wires 12a to 12d have slack therein when the power supply of the endoscope apparatus 1 is off. When the power supply of the endoscope apparatus 1 is off, the pressures of the actuators 13a to 13d are in an atmospheric pressure state. More specifically, when the pressures of the actuators 13a to 13d are in an atmospheric pressure state, the bending wires 12a to 12d have slack therein.

The actuators 13a to 13d are connected to the proximal ends of the bending wires 12a to 12d, respectively. The air tubes 14a to 14d are connected with and fixed to the proximal ends of the actuators 13a to 13d, respectively. A gas from the gas supply source 4 is supplied into the actuators 13a to 13d through the respective air tubes 14a to 14d. The actuators 13a to 13d are pneumatic artificial muscles. The actuators 13a to 13d contract when an air pressure applied thereto is high, and expand when the applied air pressure is low. In this connection, although according to the present embodiment the actuators 13a to 13d are described as pneumatic actuators that expand and contract by means of air pressure, the actuators 13a to 13d may be fluid pressure actuators that expand and contract by means of a fluid pressure such as a gas other than air or a liquid. In such a case, the endoscope apparatus 1 may have a configuration that uses a fluid supply source instead of the gas supply source 4.

As described above, the proximal ends of the actuators 13a to 13d are fixed to the air tubes 14a to 14d, respectively. Hence, when the actuators 13a to 13d contract, the respective bending wires 12a to 12d are pulled, and in contrast, when the actuators 13a to 13d expand, the respective bending wires 12a to 12d are relaxed. As a result, the bending portion 11 bends in a desired direction.

The first electromagnetic valves 15a to 15d and the second electromagnetic valves 16a to 16d are provided between the air tubes 14a to 14d and the gas supply source 4. The first electromagnetic valves 15a to 15d and the second electromagnetic valves 16a to 16d open and close in accordance with the control of the control section 17. The first electromagnetic valve 15a and the second electromagnetic valve 16a for the U direction, the first electromagnetic valve 15b and the second electromagnetic valve 16b for the D direction, the first electromagnetic valve 15c and the second electromagnetic valve 16c for the R direction, and the first electromagnetic valve 15d and the second electromagnetic valve 16d for the L direction constitute pressure adjusting sections that adjust pressures applied to the actuators 13a to 13d, respectively.

When the power supply is turned on, the control section 17 controls opening and closing of the first electromagnetic valves 15a to 15d and the second electromagnetic valves 16a to 16d, and when the power supply is turned off, the control section 17 performs pressurization of the actuators 13a to 13d so that only an amount corresponding to a length of slack of the bending wires 12a to 12d is pulled. Hereunder, performance of an operation to pressurize the actuators 13a to 13d so that only an amount corresponding to a length of slack of the bending wires 12a to 12d is pulled is also referred to as an "initial pressurization process". As a result, as shown in FIG. 2B, the actuators 13a to 13d contract and the slack of the bending wires 12a to 12d disappears. More specifically, as the result of the initial pressurization process, the bending wires 12a to 12d and an insertion axis direction of the insertion portion 2 become substantially parallel. Note that although tension is not applied to the bending wires 12a to 12d in the initial pressurization process since only an amount corresponding to a length of slack of the bending wires 12a to 12d is pulled, a configuration may also be adopted in which the actuators 13a to 13d are pressurized so as to pull the bending wires 12a to 12d by an amount that is equal to or greater than the length of slack thereof to thereby apply tension to the bending wires 12a to 12d.

Further, although pressure is applied in an equal manner to all of the actuators 13a to 13d in the initial pressurization process, a configuration may also be adopted in which pressure is not applied in an equal manner to all of the actuators 13a to 13d. According to the present embodiment, the U direction and the D direction are a pair, and the R direction and the L direction are a pair. More specifically, the bending wire 12a, the actuator 13a, the air tube 14a, and the electromagnetic valves 15a and 16a of the U direction and the bending wire 12b, the actuator 13b, the air tube 14b, and the electromagnetic valves 15b and 16b of the D direction are paired. Likewise, the bending wire 12c, the actuator 13c, the air tube 14c, and the electromagnetic valves 15c and 16c of the R direction and the bending wire 12d, the actuator 13d, the air tube 14d, and the electromagnetic valves 15d and 16d of the L direction are paired. Therefore, the bending portion 11 can be made to enter a straight line state by pressurizing so that the pressures of the actuators 13a and 13b for the U and D directions that are paired become equal, and pressurizing so that the pressures of the actuators 13c and 13d for the R and L directions that are paired become equal.

Furthermore, according to the initial pressurization process, an initial pressurization process need not be performed with respect to all of the actuators 13a to 13d. For example, the responsiveness when bending the bending portion 11 in at least one direction can be enhanced by performing an initial pressurization process with respect to the actuators 13a and 13b for the U and D directions that are paired.

An operation amount of the operation section 6, in this case a tilted amount of a joystick, for performing a bending operation or the like is supplied from the operation section 6 to the control section 17. In accordance with the operation amount supplied from the operation section 6, the control section carries out bending control that controls a bending direction, a bending speed, a bending angle and the like. In order to carry out the bending control, the control section 17 controls opening and closing of the first electromagnetic valves 15a to 15d and the second electromagnetic valves 16a to 16d, and pressurizes or depressurizes the actuators 13a to 13d.

When pressurizing the actuators 13a to 13d, the control section 17 controls the first electromagnetic valves 15a to 15d and the second electromagnetic valves 16a to 16d so as to form a channel between the gas supply source 4 and each of the actuators 13a to 13d, and feeds a gas from the gas supply source 4 to pressurize each of the actuators 13a to 13d. In contrast, when depressurizing the actuators 13a to 13d, the control section 17 controls the first electromagnetic valves 15a to 15d and the second electromagnetic valves 16a to 16d so as to form a channel between the actuators 13a to 13d and an exhaust port R (see FIG. 5 and the like), which is described later, of each of the first electromagnetic valves 15a to 15d, and releases gas from the actuators 13a to 13d to thereby depressurize the actuators 13a to 13d.

For example, as shown in FIG. 2C, when bending the bending portion 11 in the U direction, the control section 17 controls the electromagnetic valves 15a and 16a so as to pressurize the actuator 13a for the U direction, and controls the electromagnetic valves 15b and 16b so as to depressurize the actuator 13b for the D direction. As a result, since the actuator 13a for the U direction contracts and the actuator 13b for the D direction expands, the bending portion 11 bends in the U direction.

The control section 17 calculates the pressures of the actuators 13a to 13d based on the opening/closing time periods of the first electromagnetic valves 15a to 15d and the second electromagnetic valves 16a to 16d. In this connection, a configuration may also be adopted in which four pressure sensors corresponding to the upward, downward, right, and left directions are provided between the air tubes 14a to 14d and the electromagnetic valves 15a to 15d, respectively, so as to measure the pressures of the actuators 13a to 13d. In such a case, the control section 17 controls opening and closing of the first electromagnetic valves 15a to 15d and the second electromagnetic valves 16a to 16d based on pressure values from the four pressure sensors to thereby control the pressures of the actuators 13a to 13d.

Further, when a control signal that indicates that the neutral button 7 as a neutral operation section for returning to the neutral state has been pressed is supplied to the control section 17, the control section 17 controls opening and closing of the first electromagnetic valves 15a to 15d and the second electromagnetic valves 16a to 16d to carry out neutral control that is described later. In addition, when a control signal that indicates that the bending lock button 8 as a bending lock operation section for retaining a bent state, that is, a bending angle of the bending portion 11, has been pressed is supplied to the control section 17, the control section 17 controls opening and closing of the first electromagnetic valves 15a to 15d and the second electromagnetic valves 16a to 16d to carry out bending angle retention control that is described later.

According to the present embodiment, a software program for performing the above described initial pressurization process and the like is stored in an unshown memory provided in the endoscope main body 3. The control section 17 reads out the software program stored in the memory and executes the initial pressurization process and the like. In this connection, execution of the initial pressurization process and the like is not limited to execution by a software program, and a configuration may also be adopted in which the initial pressurization process and the like are executed by a mechanical mechanism.

The endoscope apparatus 1 of the present embodiment carries out bending control utilizing air pressure. Therefore, for example, even when the endoscope apparatus 1 of the present embodiment is applied to a drum-type endoscope apparatus that has an insertion portion of a long length, the responsiveness of the bending portion does not deteriorate.

Figure 3:
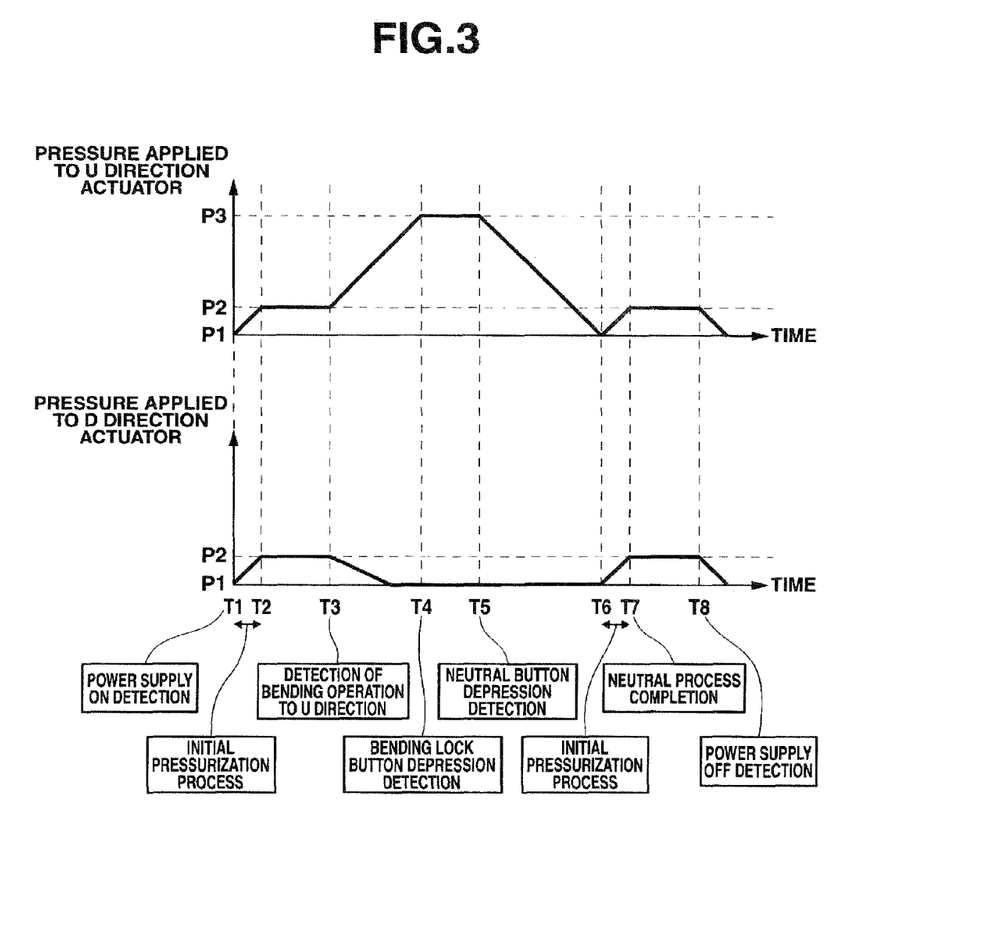
FIG. 3 is a view for describing an example of changes in pressures applied to actuators with respect to an operation example.

Next, changes in the pressures applied to the actuators 13a to 13d are described with regard to an example of operations from a time that a user turns on the power supply of the endoscope apparatus 1 until the user turns off the power supply.

FIG. 3 is a view for describing an example of changes in pressures applied to the actuators with respect to the operation example. Note that although only operations relating to the U and D directions are illustrated in FIG. 3, a similar description as that of the operations for the U and D directions applies with respect to the R and L directions.

First, at a time T1, the user turns on the power supply of the endoscope apparatus 1. Upon detecting that the power supply of the endoscope apparatus 1 is on, the control section 17 carries out an initial pressurization process that pressurizes all of the actuators 13a to 13d to a pressure for initial pressurization P2 from an atmospheric pressure P1 until reaching a time T2. The control section 17 then retains the pressure of the actuators 13a to 13d at the pressure for initial pressurization P2. A value of the pressure for initial pressurization P2 is stored in an unshown memory that is provided in the endoscope main body 3. A configuration may also be adopted in which the value of the pressure for initial pressurization P2 can be changed by the user.

Next, at a time T3, the user operates the operation section 6 that is a joystick or the like to perform a bending operation in the U direction. Upon detecting the bending operation in the U direction, the control section 17 pressurizes the actuator 13a for the U direction up to a predetermined pressure P3 that is in accordance with the operation amount of the operation section 6, and depressurizes the actuator 13b for the D direction as far as a predetermined pressure, in this case the atmospheric pressure P1, that is in accordance with the operation amount of the operation section 6.

Next, at a time T4, when a bending angle at which a desired observation can be carried out is reached, the user presses the bending lock button 8 to perform a bending lock operation that retains the bending angle of the bending portion 11. Upon detecting that the bending lock button 8 has been pressed, the control section 17 controls the first electromagnetic valve 15a and the second electromagnetic valve 16a for the U direction so as to maintain the pressure of the actuator 13a, and controls the first electromagnetic valve 15b and the second electromagnetic valve 16b for the D direction so as to maintain the pressure of the actuator 13b.

Next, at a time T5, the user presses the neutral button 7 to perform a neutral operation that temporarily returns the bending angle to zero. Upon detecting that the neutral button 7 has been pressed, the control section 17 carries out the neutral process. First, the control section 17 depressurizes all of the actuators 13a to 13d until the pressures applied to all of the actuators 13a to 13d becomes equal to or less than the pressure for initial pressurization P2, that is, equal to or less than a pressure at which the slack of the bending wires 12a and 12b disappears. According to the present embodiment, the control section 17 performs depressurization until the pressures applied to all of the actuators 13a to 13d become the atmospheric pressure P1. Subsequently, at a time T6, when all of the actuators 13a to 13d are depressurized to the atmospheric pressure P1, the control section 17 performs the initial pressurization process, and at a time T7, the control section 17 completes the neutral process.

Thereafter, the user repeats the above described bending operation, bending lock operation, and neutral operation to perform a desired examination. Finally, at a time T8, the user turns off the power supply of the endoscope apparatus 1. Upon detecting that the power supply of the endoscope apparatus 1 has been turned off, the control section 17 performs depressurization until the pressures applied to all of the actuators 13a to 13d become the atmospheric pressure P1, and then ends the process.

The control states of the first electromagnetic valves 15a to 15d and the second electromagnetic valves 16a to 16d will now be described using FIG. 4 to FIG. 7.

Figure 4:
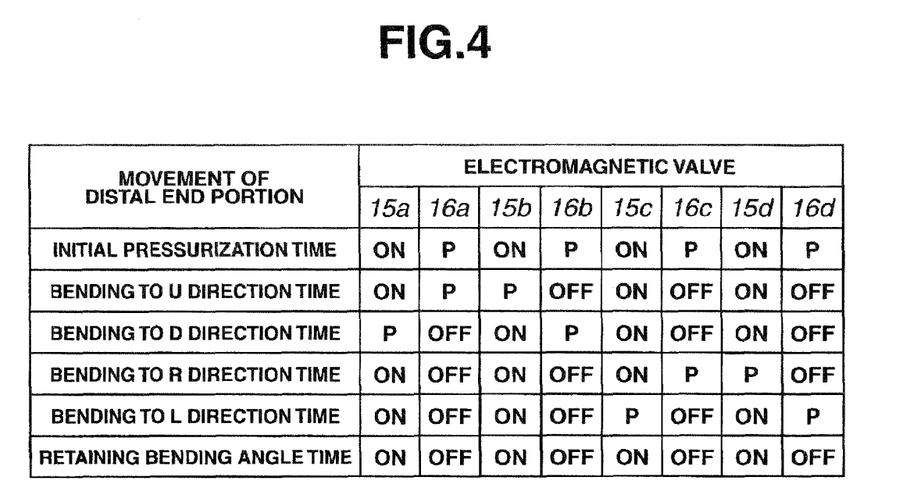
FIG. 4 is a view for describing a relationship between movement of a distal end portion and control states of electromagnetic valves.
Figure 5:
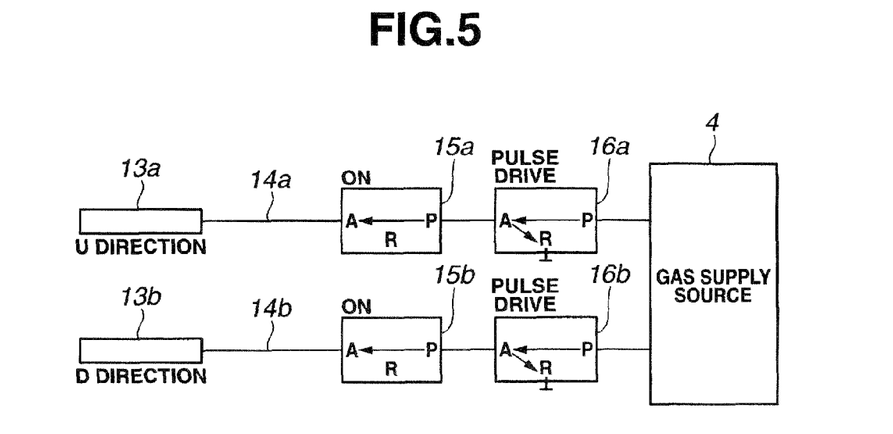
FIG. 5 is a view for describing control states of electromagnetic valves when performing an initial pressurization process.
Figure 6:
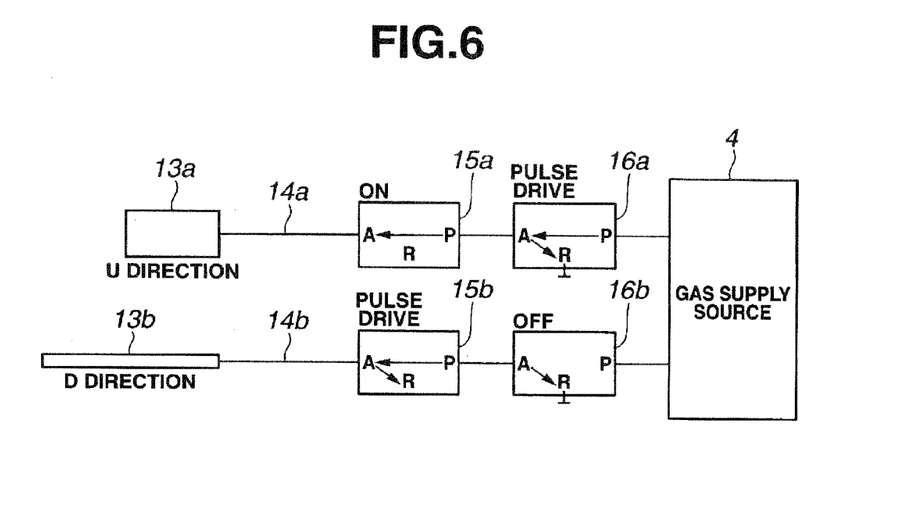
FIG. 6 is a view for describing control states of electromagnetic valves when performing a bending operation in the U direction.
Figure 7:
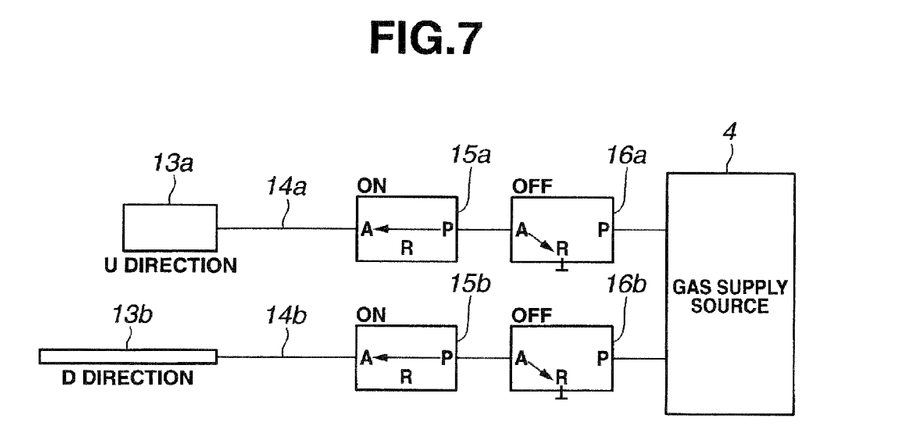
FIG. 7 is a view for describing control states of electromagnetic valves when performing an operation to retain a bending angle.

FIG. 4 is a view for describing a relationship between movement of the distal end portion and control states of the electromagnetic valves. FIG. 5 is a view for describing control states of the electromagnetic valves when performing the initial pressurization process. FIG. 6 is a view for describing control states of the electromagnetic valves when performing a bending operation in the U direction. FIG. 7 is a view for describing control states of the electromagnetic valves when performing an operation to retain a bending angle. Note that although only illustrations regarding the U and D directions are shown in FIG. 5 to FIG. 7, a similar description as that for the U and D directions applies with respect to the R and L directions.

As shown in FIG. 5 to FIG. 7, the first electromagnetic valves 15a to 15d and the second electromagnetic valves 16a to 16d are three-port electromagnetic valves that each has a valve inlet P, a valve outlet A, and an exhaust port R. However, an opening of the respective exhaust ports R of the second electromagnetic valves 16a to 16d is blocked.

An "on" state of an electromagnetic valve shown in FIG. 4 indicates that a channel for air is formed between the valve inlet P and the valve outlet A. An "off" state of an electromagnetic valve shown in FIG. 4 indicates that a channel for air is formed between the valve outlet A and the exhaust port R. Further, a "P" state of an electromagnetic valve shown in FIG. 4 represents pulse-driving that repeats the above described "on" and "off" states, and this indicates that a channel between the valve inlet P and the valve outlet A and a channel between the valve outlet A and the exhaust port R are alternately formed. A bending angle of the bending portion 11 can be gradually increased or decreased by means of the pulse-driving.

As shown in FIG. 5, when the power supply of the endoscope apparatus 1 is turned on or the neutral button 7 is pressed by the user, the control section 17 switches the first electromagnetic valve 15a for the U direction "on", and pulse-drives the second electromagnetic valve 16a. Further, the control section 17 switches the first electromagnetic valve 15b for the D direction "on", and pulse-drives the second electromagnetic valve 16b.

Because the first electromagnetic valve 15a for the U direction is "on", a channel for air is formed between the gas supply source 4 and the actuator 13a during a period in which the second electromagnetic valve 16a for the U direction that is being pulse-driven is "on", and therefore the pressure of the actuator 13a rises and the actuator 13a for the U direction contracts.

Likewise, because the first electromagnetic valve 15b for the D direction is "on", a channel for air is formed between the gas supply source 4 and the actuator 13b during a period in which the second electromagnetic valve 16b for the D direction that is being pulse-driven is "on", and therefore pressure of the actuator 13b rises and the actuator 13b for the D direction contracts. In particular, in the initial pressurization, the first electromagnetic valves 15a and 15b and the second electromagnetic valves 16a and 16b are controlled so that the pressures of the actuators 13a and 13b become the pressure for initial pressurization P2 and the slack of the bending wires 12a and 12b disappears.

As shown in FIG. 6, when the user operates the operation section 6 to instruct that a bending operation be performed in the U direction, the control section 17 switches the first electromagnetic valve 15a for the U direction "on" and pulse-drives the second electromagnetic valve 16a. The control section 17 also pulse-drives the first electromagnetic valve 15b for the D direction and switches the second electromagnetic valve 16b "off".

Because the first electromagnetic valve 15a for the U direction is "on", a channel for air is formed between the gas supply source 4 and the actuator 13a during a period in which the second electromagnetic valve 16a for the U direction that is being pulse-driven is "on", and therefore the pressure of the actuator 13a rises and the actuator 13a for the U direction contracts.

Further, during a period in which the first electromagnetic valve 15b for the D direction that is being pulse-driven is "off", a channel is formed between the actuator 13b and the exhaust port R of the first electromagnetic valve 15b for the D direction, and therefore the pressure of the actuator 13b decreases and the actuator 13b for the D direction expands. Therefore, since the actuator 13a for the U direction contracts and the actuator 13b for the D direction expands, the bending portion 11 bends in the U direction.

As shown in FIG. 7, when the user presses the bending lock button 8 to instruct that the bending angle be retained, the control section 17 switches the first electromagnetic valve 15a for the U direction "on" and switches the second electromagnetic valve 16a "off". Further, the control section 17 switches the first electromagnetic valve 15b for the D direction "on" and switches the second electromagnetic valve 16b "off".

Thus, a state is entered in which a channel is not formed between the gas supply source 4 and the actuator 13a, and a channel is also not formed between the actuator 13a and the exhaust port R of the first electromagnetic valve 15a for the U direction, and thus air is retained in the actuator 13a.

Likewise, a state is entered in which a channel is not formed between the gas supply source 4 and the actuator 13b, and a channel is also not formed between the actuator 13b and the exhaust port R of the first electromagnetic valve 15b for the D direction, and thus air is retained in the actuator 13b. Thus, air is retained in the actuators 13a and 13b. More specifically, since the pressures of the actuators 13a and 13b do not change, the bending angle of the bending portion 11 is retained.

Next, respective processes of the endoscope apparatus 1 are described using FIG. 8 to FIG. 12. The respective processes shown in FIG. 8 to FIG. 12 are executed by the control section 17.

Figure 8:
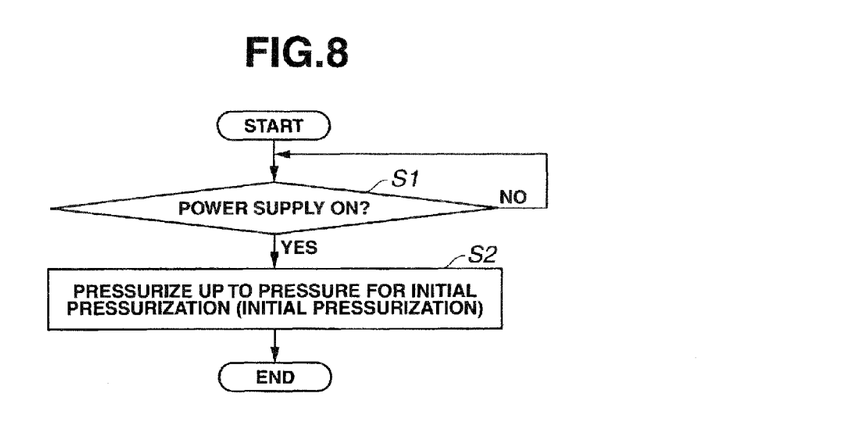

FIG. 8 is a flowchart for describing an example of a process flow when the power supply of the endoscope apparatus is turned on.

First, the control section 17 detects whether or not the power supply of the endoscope apparatus 1 has been turned on (step S1). If the power supply of the endoscope apparatus 1 has not been turned on, "no" is determined as the detection result and the process returns to step S1. In contrast, if the power supply of the endoscope apparatus 1 has been turned on initial pressurization is carried out, that is, all of the actuators 13a to 13d are pressurized until the pressures applied thereto reach the pressure for initial pressurization P2 (step S2), and thereafter the control section 17 ends the process.

Figure 9:
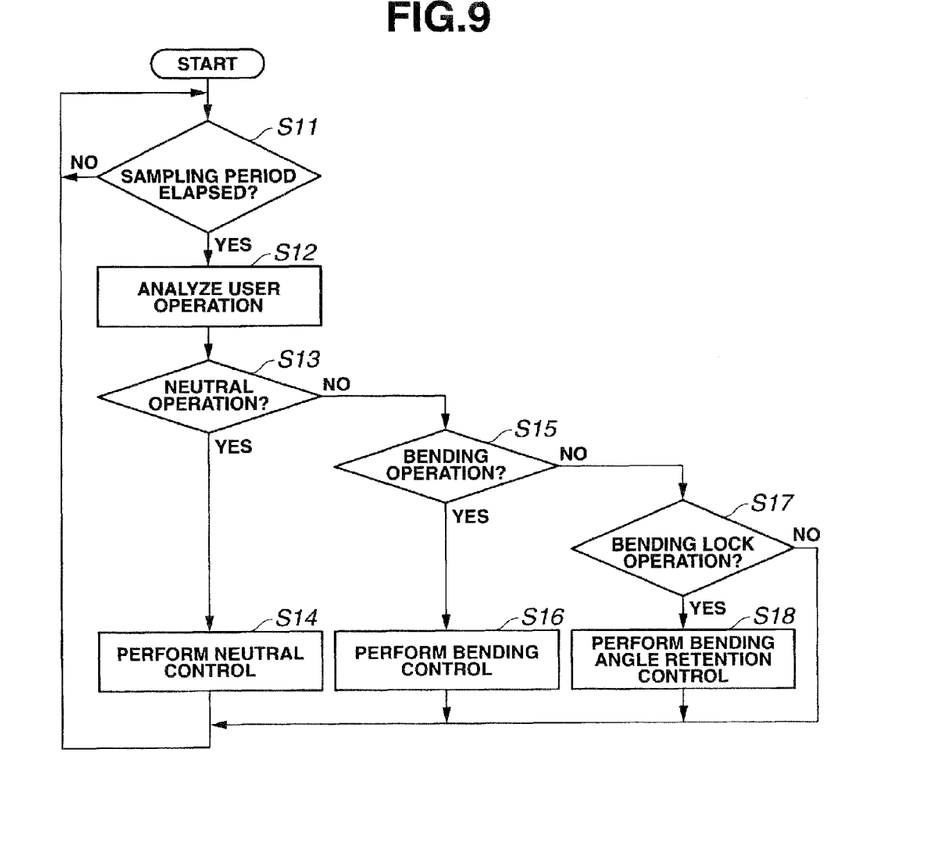
FIG. 9 is a flowchart for describing an example of a flow of a bending control process that uses air pressure.

FIG. 9 is a flowchart for describing an example of the flow of a process in which bending control is performed using air pressure.

First, the control section 17 detects whether or not a sampling period has elapsed (step S11). If the sampling period has not elapsed, "no" is determined as the detection result and the process returns to step S11 to repeat the same process. In contrast, if the sampling period has elapsed, a user operation is analyzed (step S12). In the analysis in step S12, it is determined if the user has performed a bending operation by operating the operation section 6, a neutral operation by pressing the neutral button 7, or a bending lock operation by pressing the bending lock button 8.

Next, the control section 17 detects whether or not the user operation is a neutral operation (step S13). If the user operation is a neutral operation, the determined result is "yes", and therefore the control section 17 performs neutral control (step S14). Thereafter, the operation returns to step S11 to repeat the same process. In contrast, in step S13, if the user operation is not a neutral operation, the determined result is "no", and the control section 17 then detects whether or not the user operation is a bending operation (step S15). If the user operation is a bending operation, the determined result is "yes", and therefore the control section 17 performs bending control (step S16). Thereafter, the operation returns to step S11 to repeat the same process. In contrast, in step S15, if the user operation is not a bending operation, the determined result is "no", and the control section 17 then detects whether or not the user operation is a bending lock operation (step S17). If the user operation is a bending lock operation, a bending angle retention process is performed (step S18). Thereafter, the operation returns to step S11 to repeat the same process. In contrast, if the user operation is not a bending lock operation, the determined result is "no", and therefore the operation returns to step S11 to repeat the same process.

Figure 10:
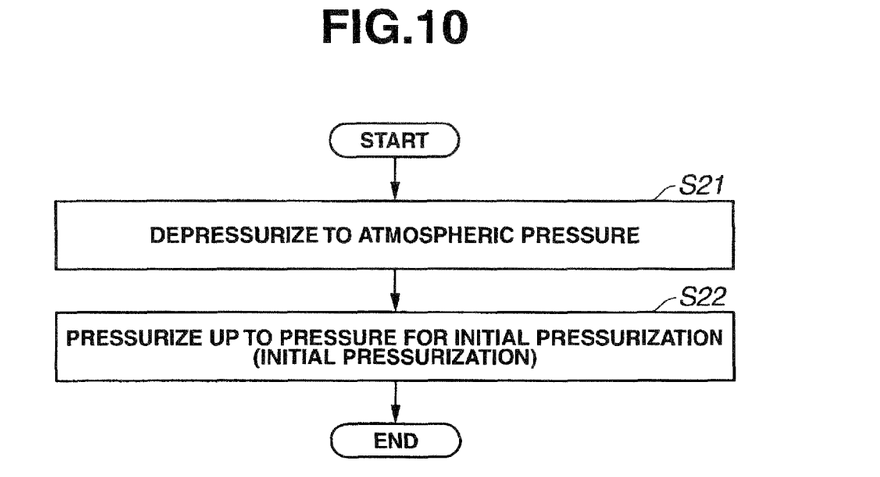
FIG. 10 is a flowchart for describing an example of a flow of a neutral control process.

Next, the neutral control process in step S14 will be described.

FIG. 10 is a flowchart for describing an example of the flow of the neutral control process.

First, the pressures applied to all of the actuators 13a to 13d are depressurized to the atmospheric pressure P1 (step S21). When the pressures applied to all of the actuators 13a to 13d are depressurized to the atmospheric pressure P1, the control section 17 executes the initial pressurization process, that is, the control section 17 pressurizes all of the actuators 13a to 13d until the pressures applied thereto reach the initial pressurization P2 (step S22), and thereafter ends the process.

Figure 11:
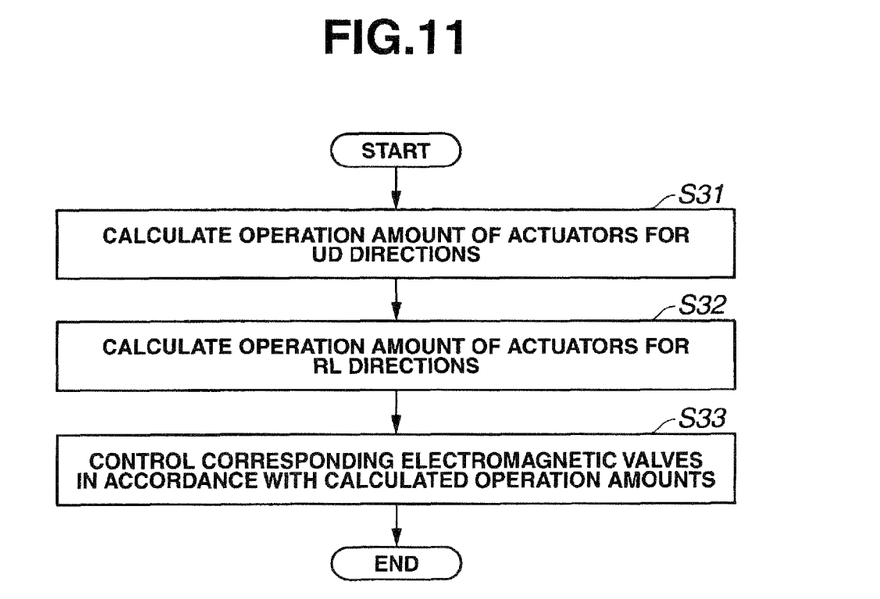
FIG. 11 is a flowchart for describing an example of a flow of a bending control process.

Next, the bending control process in step S16 will be described.

FIG. 11 is a flowchart for describing an example of the flow of the bending control process.

First, the control section 17 calculates the operation amounts of the actuators 13a and 13b for the U and D directions (step S31). Next, the control section 17 calculates the operation amounts of the actuators 13c and 13d for the R and L directions (step S32). Finally, the control section 17 controls the corresponding electromagnetic valves in accordance with the operation amounts calculated in steps S31 and S32 (step S33), and thereafter ends the process.

Figure 12:
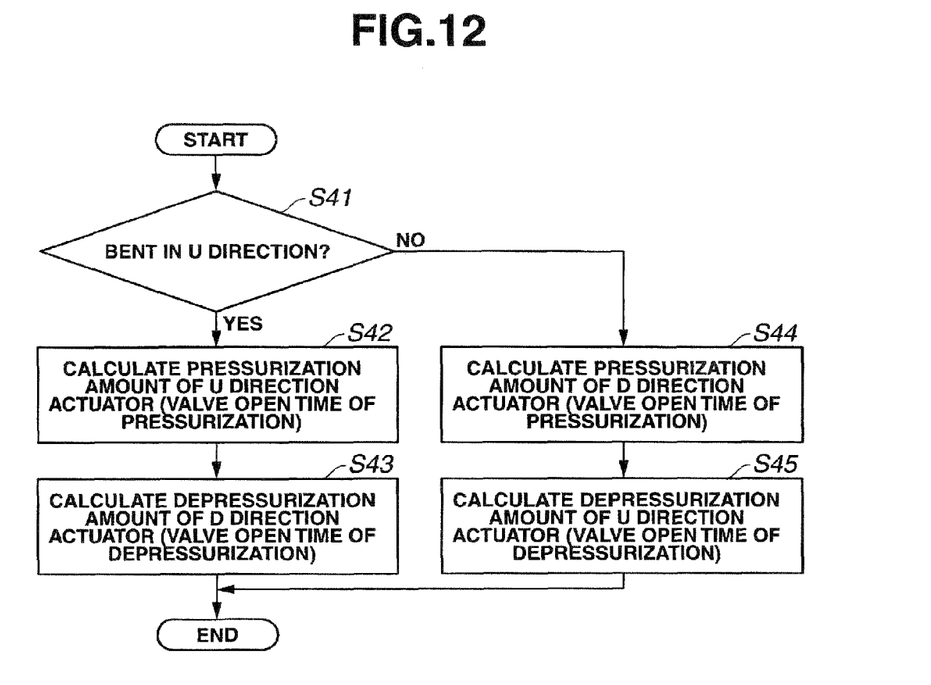
FIG. 12 is a flowchart for describing an example of a flow of a process that calculates operation amounts of the actuators for the U and D directions.

Next, the process of calculating the operation amounts of the actuators 13a and 13b for the U and D directions in step S31 is described.

FIG. 12 is a flowchart for describing an example of the flow of the process that calculates the operation amounts of the actuators for the U and D directions.

First, the control section 17 detects whether or not bending is being performed in the U direction (step S41). If bending is being performed in the U direction, "yes" is determined as the detection result, and the control section 17 calculates a pressurization amount of the actuator 13a in the U direction (step S42). In this process in step S42, the control section 17 calculates the pressurization amount of the actuator 13a for the U direction by detecting a time period for which a channel has been formed between the gas supply source 4 and the actuator 13a. Subsequently, the control section 17 calculates a depressurization amount of the actuator 13b for the D direction (step S43), and then ends the process. In the process in step S43, the control section 17 calculates the depressurization amount of the actuator 13b for the D direction by detecting a time period for which a channel has been formed between the actuator 13b and the exhaust port R of the first electromagnetic valve 15b for the D direction.

In contrast, in step S41, if bending is not being performed in the U direction, "no" is determined as the detection result, and the operation proceeds to step S44. More specifically, if bending is not being performed in the U direction, the control section 17 determines that bending is being performed in the D direction, and calculates a pressurization amount of the actuator 13b for the D direction (step S44). In the process in step S44, the control section 17 calculates the pressurization amount of the actuator 13b for the D direction by detecting a time period for which a channel has been formed between the gas supply source 4 and the actuator 13b. Subsequently, the control section 17 calculates a depressurization amount of the actuator 13a for the U direction (step S45), and ends the process. In the process in step S45, the control section 17 calculates the depressurization amount of the actuator 13a for the U direction by detecting a time period for which a channel has been formed between the actuator 13a and the exhaust port R of the first electromagnetic valve 15a for the U direction.

As described above, when the power supply of the endoscope apparatus 1 is turned on or the neutral button 7 is pressed, the initial pressurization process is performed and the actuators 13a to 13d are pressurized so as to remove the slack in the bending wires 12a to 12d. Thus, in the endoscope apparatus 1, when the user operates the operation section 6 to input an instruction to perform a bending operation, a response can be obtained that is equivalent to that at a time when there is no slack in the bending wires.

Further, in the endoscope apparatus 1, when the user operates the operation section 6 to input an instruction to perform a bending operation, since an actuator on the opposite side to the bending direction is depressurized, the depressurized actuator expands and the slack in the bending wire is retained. Therefore, the slack in the bending wires 12a to 12d is utilized effectively so that the bending angle of the bending portion 11 can be bent as far as the maximum angle to which the actuators 13a to 13d can bend the bending portion 11.

Hence, according to the endoscope apparatus of the present embodiment, the responsiveness of the bending portion can be improved without lowering the performance with respect to the maximum bending angle of the bending portion.

MODIFICATION EXAMPLE

Next, a modification example of the above described embodiment will be described.

Figure 13:
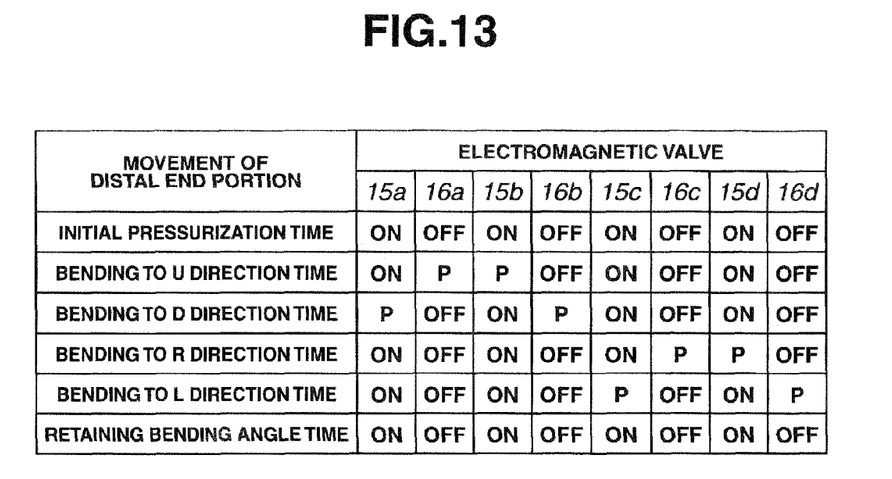
FIG. 13 is a view for describing a relationship between movement of a distal end portion and control states of electromagnetic valves according to a modification example of the endoscope apparatus of the embodiment.
Figure 14:
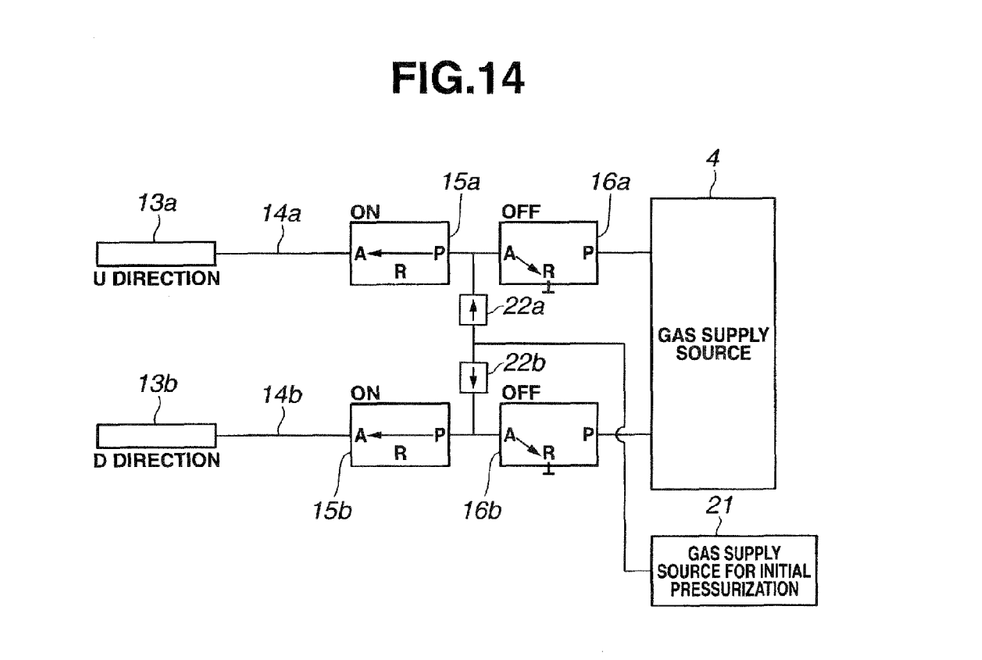
FIG. 14 is a view for describing control states of electromagnetic valves when performing an initial pressurization process according to the modification example of the endoscope apparatus of the embodiment.
Figure 15:
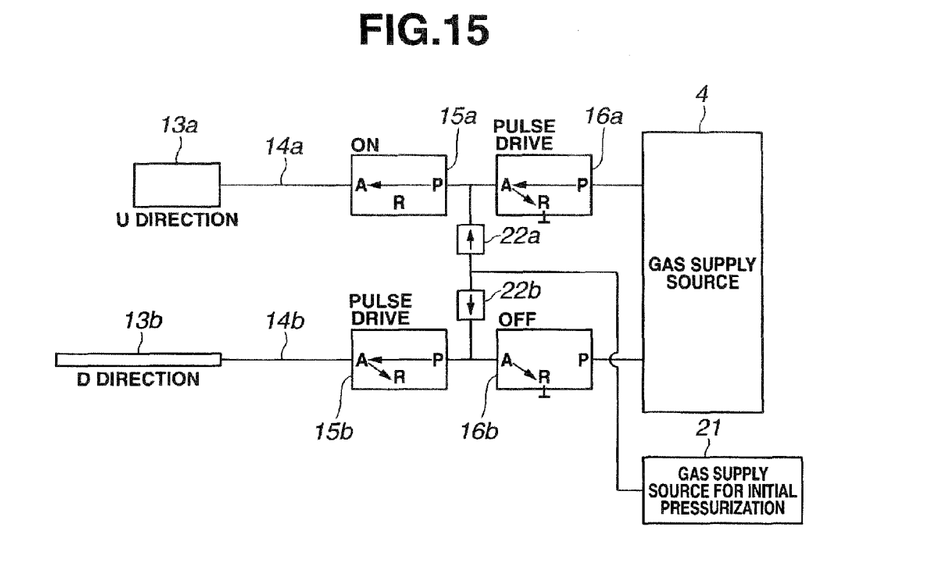
FIG. 15 is a view for describing control states of electromagnetic valves when performing a bending operation in the U direction according to the modification example of the endoscope apparatus of the embodiment.
Figure 16:
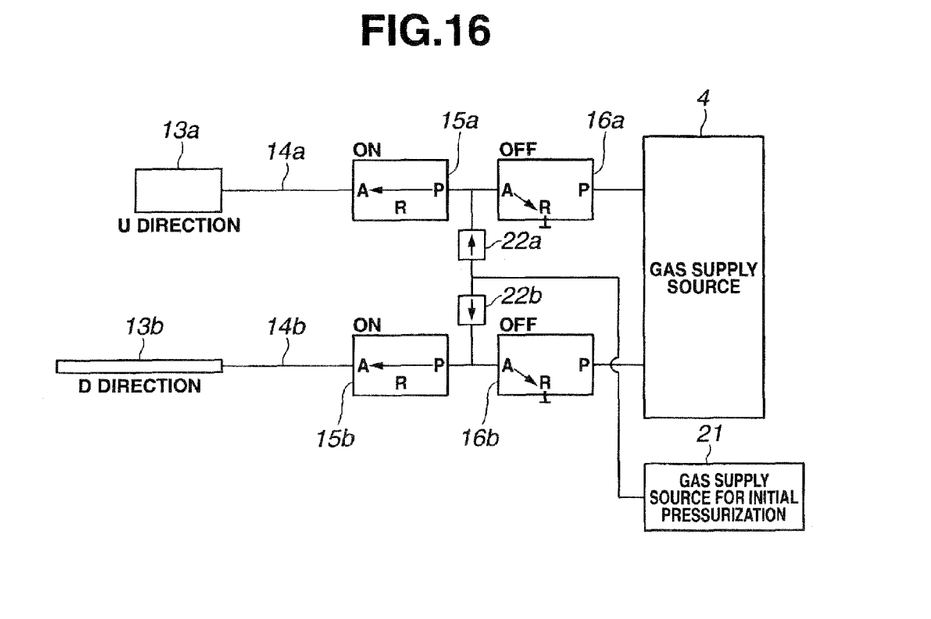
FIG. 16 is a view for describing control states of electromagnetic valves when performing an operation to retain a bending angle according to the modification example of the endoscope apparatus of the embodiment.

FIG. 13 is a view for describing the relationship between movement of the distal end portion and control states of the electromagnetic valves according to a modification example of the endoscope apparatus of the present embodiment. FIG. 14 is a view for describing control states of the electromagnetic valves when performing an initial pressurization process according to the modification example of the endoscope apparatus of the present embodiment. FIG. 15 is a view for describing control states of the electromagnetic valves when performing a bending operation in the U direction according to the modification example of the endoscope apparatus of the present embodiment. FIG. 16 is a view for describing control states of the electromagnetic valves when performing an operation to retain a bending angle according to the modification example of the endoscope apparatus of the present embodiment. In this connection, although only the U and D directions are illustrated in FIG. 14 to FIG. 16, the same configuration as that for the U and D directions also applies with respect to the R and L directions.

As shown in FIG. 14 to FIG. 16, according to the present modification example, a gas supply source for initial pressurization 21, and check valves 22a to 22d corresponding to the upward, downward, right, and left directions, respectively, are provided in the endoscope apparatus. In this connection, only the U and D directions are illustrated in FIG. 14 to FIG. 16.

According to the present modification example, when an initial pressurization process is performed, air is supplied to the actuators 13a to 13d from the gas supply source for initial pressurization 21.

The check valves 22a to 22d are valves through which air can flow in only the directions of the arrows shown in FIG. 14 to FIG. 16. With respect to the two ends of the check valves 22a to 22d, when the pressure on the electromagnetic valves 15a to 15d side is higher than the pressure of the gas supply source for initial pressurization 21, air does not flow to the actuators 13a to 13d from the gas supply source for initial pressurization 21. In contrast, when the pressure on the electromagnetic valves 15a to 15d side is lower than the pressure of the gas supply source for initial pressurization 21, air flows from the gas supply source for initial pressurization 21 in the direction of the arrows to the actuators 13a to 13d until the actuators 13a to 13d reach the pressure for initial pressurization P2.

Thus, at the time of the initial pressurization process, air is supplied to the actuators 13a to 13d from the gas supply source for initial pressurization 21. Consequently, as shown in FIG. 13, at the time of the initial pressurization process, the electromagnetic valves 16a to 16d are "off" so that a channel is not formed between the gas supply source 4 and the actuators 13a to 13d.

As shown in FIG. 14, when the user turns on the power supply or presses the neutral button 7 to instruct that neutral control be performed, the control section 17 switches the electromagnetic valve 15a for the U direction "on" and switches the electromagnetic valve 16a for the U direction "off". The control section 17 also switches the electromagnetic valve 15b for the D direction "on" and switches the electromagnetic valve 16b for the D direction "off".

During a period in which the electromagnetic valve 15a for the U direction is "on", a channel for air is formed between the gas supply source for initial pressurization 21 and the actuator 13a, and the pressure of the actuator 13a rises and thus the actuator 13a for the U direction contracts.

Likewise, during a period in which the electromagnetic valve 15b for the D direction is "on", a channel for air is formed between the gas supply source for initial pressurization 21 and the actuator 13b, and the pressure of the actuator 13b rises and thus the actuator 13b for the D direction contracts.

As shown in FIG. 15, when the user operates the operation section 6 to input an instruction to perform a bending operation in the U direction, the control section 17 switches the electromagnetic valve 15a for the U direction "on" and pulse-drives the electromagnetic valve 16a. Further, the control section 17 pulse-drives the electromagnetic valve 15b for the D direction and switches the electromagnetic valve 16b for the D direction "off".

During a period in which the electromagnetic valve 16a for the U direction that is being pulse-driven is "on", a channel for air is formed between the gas supply source 4 and the actuator 13a, and the pressure of the actuator 13a rises and thus the actuator 13a for the U direction contracts.

Further, during a period in which the electromagnetic valve 15b for the D direction that is being pulse-driven is "off", a channel is formed between the actuator 13b and the exhaust port R of the electromagnetic valve 15b, and the pressure of the actuator 13b decreases and thus the actuator 13b for the D direction expands.

Because the check valve 22a is provided, a channel is not formed between the gas supply source for initial pressurization 21 and the actuator 13a. Likewise, because the check valve 22b is provided, a channel is not formed between the gas supply source for initial pressurization 21 and the actuator 13b.

As shown in FIG. 16, when the user presses the bending lock button 8 to input an instruction to retain the bending angle, the control section 17 switches the electromagnetic valve 15a for the U direction "on" and switches the electromagnetic valve 16a for the U direction "off". Further, the control section 17 switches the electromagnetic valve 15b for the D direction "on" and switches the electromagnetic valve 16b for the D direction "off".

Thus, a state is entered in which a channel is not formed between the gas supply source 4 and the actuator 13a, and a channel is also not formed between the actuator 13a and the exhaust port R of the electromagnetic valve 15a, and therefore air is confined in the actuator 13a.

Likewise, a state is entered in which a channel is not formed between the gas supply source 4 and the actuator 13b, and a channel is also not formed between the actuator 13b and the exhaust port R of the electromagnetic valve 15b, and therefore air is confined in the actuator 13b. Thus, air is retained in the actuators 13a and 13b. More specifically, since the pressures of the actuators 13a and 13b do not change, the bending angle is retained.

Because the check valve 22a is provided, a channel is not formed between the gas supply source for initial pressurization 21 and the actuator 13a. Likewise, because the check valve 22b is provided, a channel is not formed between the gas supply source for initial pressurization 21 and the actuator 13b.

According to the endoscope apparatus of the present modification example, similarly to the above described embodiment, the responsiveness of the bending portion can be improved without lowering the performance with respect to the maximum bending angle of the bending portion.

It is to be noted that with respect to each step in each flowchart of the present specification, the order of executing each step may be altered, steps may be executed simultaneously, or steps may be executed in a different order at each execution, as long as such execution is not contrary to the essential nature thereof.

The present invention is not limited to the above described embodiment, and various changes and modifications are possible without departing from the scope and spirit of the invention.

What is claimed is:

1. An endoscope apparatus, comprising:
a bending portion that bends in at least one direction;
an operation portion which is operable by a user to input an instruction to return the bending portion to a neutral state;
two bending wires that are each connected to the bending portion;
two actuators that are connected to proximal ends of the two bending wires, respectively, and that contract or expand by means of a gas pressure;
a first electromagnetic valve connected to one of the two actuators;
a second electromagnetic valve connected to the first electromagnetic valve;
a third electromagnetic valve connected to the other of the two actuators;
a fourth electromagnetic valve connected to the third electromagnetic valve;
a gas supply source that is connected to the second and fourth electromagnetic valves and supplies a gas to the two actuators; and
a control section that controls the first, second, third and fourth electromagnetic valves;
wherein:
each of the two bending wires has slack therein when the two actuators are in an atmospheric pressure state;
in response to the instruction to return the bending portion to the neutral state, the control section controls the first, second, third and fourth electromagnetic valves so as to put the two actuators in the atmospheric pressure state in which each of the two bending wires has slack, and then controls the first, second, third and fourth electromagnetic valves to perform an initial pressurization in which the two actuators are pressurized to an initial pressurization pressure at which the slack of each of the two bending wires disappears and the bending portion is not bent, the initial pressurization pressure being greater than atmospheric pressure; and the neutral state is a state in which the two actuators are pressurized to the initial pressurization pressure at which the slack of each of the bending wires disappears and the bending portion is not bent.

2. The endoscope apparatus according to claim 1, further comprising:
further operation section that is configured to instruct performance of a bending operation of the bending portion;
wherein the control section controls the first, second, third and fourth electromagnetic valves so as to pressurize or depressurize the two actuators based on an operation instruction from the further operation section.

3. The endoscope apparatus according to claim 1, further comprising:
a bending lock operation section that is configured to instruct retention of a bending angle of the bending portion;
wherein, when the bending lock operation section is operated, the control section controls the first, second, third and fourth electromagnetic valves so as to retain pressures of the two actuators.

4. The endoscope apparatus according to claim 1, wherein the control section is configured to perform the initial pressurization in response to turning on of a power supply of the endoscope apparatus.

5. The endoscope apparatus according to claim 1,
wherein when a power supply of the endoscope apparatus is turned on, the control section turns on the first and third electromagnetic valves and pulse-drives the second and fourth electromagnetic valves, to thereby provide the gas from the gas supply source to the two actuators and subject the two actuators to the initial pressurization.

6. The endoscope apparatus according to claim 1, comprising:
a first check valve connected between the first electromagnetic valve and the second electromagnetic valve;
a second check valve connected between the third electromagnetic valve and the fourth electromagnetic valve; and
a gas supply source for the initial pressurization connected to the first and second check valves; and
wherein when a power supply of the endoscope apparatus is turned on, the control section turns on the first and third electromagnetic valves and turns off the second and fourth electromagnetic valves, to thereby provide gas from the gas supply source for the initial pressurization to the two actuators and subject the two actuators to the initial pressurization.

7. An endoscope apparatus, comprising:
a power supply;
a bending portion that bends in at least one direction;
bending wires that are respectively provided to correspond to two orientations in one bending direction of the bending portion and comprise a first bending wire corresponding to a first orientation in the one bending direction and having a distal end connected to the bending portion and a second bending wire corresponding to a second orientation in the one bending direction and having a distal end connected to the bending portion;
actuators which contract or expand due to a pressure of a gas supplied thereto and which pull the bending wires by contracting, wherein the actuators comprise a first actuator connected to a proximal end of the first bending wire and a second actuator connected to a proximal end of the second bending wire;

a gas supply source that supplies the gas to the first and second actuators, the first and second bending wires being disposed to have slack when the power supply of the apparatus is off;

a first electromagnetic valve connected to the first actuator;

a second electromagnetic valve connected to the first electromagnetic valve and the gas supply source;

a third electromagnetic valve connected to the second actuator;

a fourth electromagnetic valve connected to the third electromagnetic valve and the gas supply source; and a control section that detects when the power supply is turned on, and upon detecting that the power supply is turned on after being turned off, controls the first, second, third and fourth electromagnetic valves such that each of the actuators pulls the bending wire connected thereto by at least an amount corresponding to a length of the slack in the bending wire.

8. The endoscope apparatus according to claim 7, further comprising:

a memory that stores a pressure value at which each of the actuators pulls by said at least the amount corresponding to the length of the slack, wherein the control section controls the first, second, third and fourth electromagnetic valves based on the pressure value stored in the memory.

9. The endoscope apparatus according to claim 8, wherein the pressure value in the memory is changeable.

10. The endoscope apparatus according to claim 7, further comprising:

an operation section for instructing a bending operation for the bending portion, wherein the control section controls the first, second, third and fourth electromagnetic valves such that the pressure value at which each of the actuators pulls by said at least the amount corresponding to the length of the slack is retained until the bending operation from the operation section is detected.

11. The endoscope apparatus according to claim 10, wherein when the bending operation for the first orientation in the one bending direction is detected, the control section controls the third and fourth electromagnetic valves such that the second actuator corresponding to the second orientation in the one bending direction has a same pressure value as when the power supply is off.

12. The endoscope apparatus according to claim 11, wherein the pressure value when the power supply is off is an atmospheric pressure.

13. An endoscope apparatus, comprising:

a bending portion that bends in at least one direction;

an operation portion which is operable by a user to input an instruction to return the bending portion to a neutral state;

two bending wires that are each connected to the bending portion and have slack;

two actuators that are connected to proximal ends of the two bending wires, respectively, and that contract or expand by means of a gas pressure;

a first electromagnetic valve connected to one of the two actuators;

a second electromagnetic valve connected to the first electromagnetic valve;

a third electromagnetic valve connected to the other of the two actuators a fourth electromagnetic valve connected to the third electromagnetic valve;

a gas supply source that is connected to the second and fourth electromagnetic valves and supplies a gas to the two actuators; and a control section that, in response to the instruction to return the bending portion to the neutral state, controls the first, second, third, and fourth electromagnetic valves so as to put the two actuators in an atmospheric pressure state in which each of the two bending wires has slack, and then controls the first, second, third and fourth electromagnetic valves to perform an initial pressurization in which the two actuators are pressurized to an initial pressurization pressure at which the slack of each of the two bending wires disappears and the bending portion is not bent, the initial pressurization pressure being greater than atmospheric pressure;

wherein in the initial pressurization, the two actuators contract to pull only an amount of the bending wires corresponding to the slack of the bending wires; and wherein the neutral state is a state in which the two actuators are pressurized to the initial pressurization pressure at which the slack of each of the bending wires disappears and the bending portion is not bent.

14. The endoscope apparatus according to claim 13, further comprising:

a further operation section for instructing a bending operation for the bending portion;

wherein the control section controls the first, second, third and fourth electromagnetic valves so as to pressurize or depressurize the two actuators based on an operation instruction from the further operation section.

15. The endoscope apparatus according to claim 13, further comprising:

a bending lock operation section for instructing retention of a bending angle of the bending portion;

wherein, when the bending lock operation section is operated, the control section controls the first, second, third and fourth electromagnetic valves so as to retain the pressures of the two actuators.

* * * * *